United States Patent
Kerkis et al.

(10) Patent No.: US 11,020,436 B2
(45) Date of Patent: Jun. 1, 2021

(54) MULTIPOTENT AND IMMUNOCOMPATIBLE STEM CELL CONCENTRATE

(71) Applicant: REGENERA—MEDICINA VETERINÁRIA AVANÇADA LTDA., Campinas (BR)

(72) Inventors: Alexandre Kerkis, São Paulo (BR); Cristiane Valverde Wenceslau, São Paulo (BR); Michele Andrade De Barros, Campinas (BR); João Flávio Panattoni Martins, Campinas (BR)

(73) Assignee: REGENERA—MEDICINA VETERINÁRIA AVANÇADA LTDA., Campinas (BR)

( * ) Notice: Subject to any disclaimer, the term of this patent is extended or adjusted under 35 U.S.C. 154(b) by 0 days.

(21) Appl. No.: 15/108,452

(22) PCT Filed: Dec. 22, 2014

(86) PCT No.: PCT/BR2014/050054
§ 371 (c)(1),
(2) Date: Jun. 27, 2016

(87) PCT Pub. No.: WO2015/095947
PCT Pub. Date: Jul. 2, 2015

(65) Prior Publication Data
US 2016/0324899 A1 Nov. 10, 2016

(30) Foreign Application Priority Data
Dec. 27, 2013 (BR) .......................... 102013033827-3

(51) Int. Cl.
| | | |
|---|---|---|
| *A61K 35/28* | (2015.01) | |
| *C12N 5/0775* | (2010.01) | |
| *A61L 27/38* | (2006.01) | |
| *C12N 5/077* | (2010.01) | |
| *A61K 38/01* | (2006.01) | |
| *A61K 38/17* | (2006.01) | |
| *A61K 38/18* | (2006.01) | |
| *A61K 38/16* | (2006.01) | |
| *A61K 9/00* | (2006.01) | |
| *A61L 27/36* | (2006.01) | |

(52) U.S. Cl.
CPC ............ *A61K 35/28* (2013.01); *A61K 9/0019* (2013.01); *A61K 9/0048* (2013.01); *A61K 38/014* (2013.01); *A61K 38/16* (2013.01); *A61K 38/17* (2013.01); *A61K 38/18* (2013.01); *A61L 27/3604* (2013.01); *A61L 27/365* (2013.01); *A61L 27/3654* (2013.01); *A61L 27/3662* (2013.01); *A61L 27/3683* (2013.01); *A61L 27/386* (2013.01); *A61L 27/3834* (2013.01); *A61L 27/3847* (2013.01); *A61L 27/3852* (2013.01); *C12N 5/0653* (2013.01); *C12N 5/0667* (2013.01); *A61L 2300/412* (2013.01); *A61L 2300/64* (2013.01); *A61L 2430/02* (2013.01); *A61L 2430/06* (2013.01); *A61L 2430/10* (2013.01); *A61L 2430/24* (2013.01); *C12N 2506/13* (2013.01)

(58) Field of Classification Search
CPC .... A61K 35/28; A61K 9/0048; A61K 9/0019; A61L 27/3834; A61L 27/3847; A61L 27/3852; A61L 27/386; A61L 27/365; A61L 27/3654; A61L 27/3662; A61L 27/3604; A61L 27/3683; A61L 2430/02; A61L 2430/06; A61L 2430/10; A61L 2430/24; A61L 2300/64; A61L 2300/412; C12N 5/0667; C12N 2506/13
See application file for complete search history.

(56) References Cited

U.S. PATENT DOCUMENTS

| | | | |
|---|---|---|---|
| 7,429,488 B2 * | 9/2008 | Fraser .................. | C12N 5/0667 424/93.7 |
| 2008/0213235 A1 | 9/2008 | Katz et al. | |
| 2012/0094380 A1 | 4/2012 | Tzu-Bi Shin et al. | |
| 2013/0302291 A1 * | 11/2013 | Stephenne ........... | A61K 31/727 424/93.7 |

FOREIGN PATENT DOCUMENTS

EP 2 292 736 1/2015

OTHER PUBLICATIONS

Crisan et al. A Perivascular Origin for Mesenchymal Stem Cells in Multiple Human Organs. (Cell Stem Cell (2008), v3, p. 301-313.*
J. Ye. Adipose Tissue Vascularization: Its Role in Chronic Inflammation. Curr Diab Rep (2011), v11, p. 203-210. (Year: 2011).*
Stem cell. (2005). In W. G. Hale, V. A. Saunders, & J. P. Margham, Collins dictionary of biology (2nd ed.). London, UK: Collins. Retrieved from https://search.credoreference.com/content/entry/collinsbiology/stem_cell/0?institutionId=743 (Year: 2005).*
Riekstina et al. Embryonic Stem Cell Marker Expression Pattern in Human Mesenchymal Stem Cells Derived from Bone Marrow, Adipose Tissue, Heart and Dermis. Stem Cell Rev and Rep (2009), 5, 378-386. (Year: 2009).*
Mitchell et al. Immunophenotype of Human Adipose-Derived Cells: Temporal Changes in Stromal-Associated and Stem Cell-Associated Markers. Stem Cells 2006;24:376-385. (Year: 2006).*
Gao et al. Expression pattern of embryonic stem cell markers in DFAT cells and ADSCs. Mol Biol Rep (2012) 39:5791-5804. (Year: 2012).*
Peroni et al. Stem molecular signature of adipose-derived stromal cells. Experimental Cell Research 314 (2008) 603-615. (Year: 2008).*

(Continued)

*Primary Examiner* — Sean C. Barron
(74) *Attorney, Agent, or Firm* — B. Aaron Schulman, Esq.; Stites & Harbison, PLLC

(57) ABSTRACT

The present invention generally relates to a stem cell concentrate isolated from a mammalian vascularized adipose tissue, biopharmaceuticals containing such concentrate and use thereof in therapies for treating diseases in mammals.

13 Claims, 2 Drawing Sheets

(56) References Cited

OTHER PUBLICATIONS

Lin et al. Stem Cells and Development 17:1053-1064 (2008). (Year: 2008).*
Wu et al. Amniotic membrane and adipose-derived stem cell co-culture system enhances bone regeneration in a rat periodontal defect model. Journal of the Formosan Medical Association (2016) 115, 186e194. (Year: 2016).*
Li et al. miR-10a Restores Human Mesenchymal Stem Cell Differentiation by Repressing KLF4. J. Cell. Physiol. 228: 2324-2336, 2013. (Year: 2013).*
Amos et al. IFATS Collection: The Role of Human Adipose-Derived Stromal Cells in Inflammatory Microvascular Remodeling and Evidence of a Perivascular Phenotype. Stem Cells 2008;26:2682-2690. (Year: 2008).*
Written Opinion of the International Searching Authority for PCT/BR2014/050054, dated May 12, 2015.
International Search Report for PCT/BR2014/050054, dated May 12, 2015.
Written Opinion of the International Searching Authority for PCT/BR2014/050054, dated Apr. 6, 2016.
Black et al. Effect of adipose-derived mesenchymal stem and regenerative cells on lameness in dogs with chronic osteoarthritis of the coxofemoral joints: a randomized, double-blinded, multicenter, controlled trial. (abstract, p. 273).
Crisan et al. A perivascular origin for mesenchymal stem cells in multiple and human organs. Cell Stem Cell, 3: 301-313.2008. (abstract, p. 302, 303 and 306).
International Preliminary Report on Patentability in International Application No. PCT/BR2014/050054, dated Jul. 28, 2016.
Applicants Response to Written Opinion of the International Searching Authority for PCT/BR2014/050054, dated Jun. 6, 2016.
Office Action dated Apr. 25, 2017 in Canadian Application No. 2,935,211.
Black, et al., "Effect of Adipose-Derived Mesenchymal Stem and Regenerative Cells on Lameness in Dogs with Chronic Osteoarthritis of the Coxofemoral Joints: A Randomized, Double-Blinded, Multicenter, Controlled Trial", Winter 2007, pp. 272-284, vol. 8, No. 4, Veterinary Therapeutics.
Office Action dated May 21, 2020 in Canadian Application No. 2,935,211.
Linda Black, et al., "Effect of Adipose-Derived Mesenchymal Stem and Regenerative Cells on Lameness in Dogs with Chronic Osteoarthritis of the Coxofemoral Joints: A Randomized, Double-Blinded, Multicenter, Controlled Trial", Winter 2007, pp. 272-284, vol. 8, No. 4, Veterinary Therapeutics.
Brazilian Preliminary Office Action dated Jun. 2, 2020 in Brazilian Application No. BR 102013033827-3.
Zuk, et al, "Human adipose tissue is a source of multipotent stem cells", Dec. 2002, pp. 4279-4295, vol. 13, No. 12, Molecular Biology of the Cell.
Bouacida, et al, "Pericyte-like progenitors show high immaturity and engraftment potential as compared with mesenchymal stem cells", Nov. 2012, pp. 1-14, vol. 7, No. 11, Plos One.
Caplan, et al, "Mesenchymal stem cells: building blocks for molecular medicine in the $21^{st}$ century", Jun. 2001, pp. 259-264, vol. 7, No. 6, Trends in Molecular Medicine.
Black et al, "Effect of Intraarticular Injection of Autologous Adipose-Derived Mesenchymal Stem and Regenerative Cells on Clinical Signs of Chronic Osteoarthristis of the Elbow Joint in Dogs", 2008, pp. 192-200, vol. 9, No. 3, Veterinary Therapeutics.

* cited by examiner

MULTIPOTENT AND IMMUNOCOMPATIBLE STEM CELL CONCENTRATE

The present invention generally relates to a stem cell concentrate isolated from mammalian vascularized adipose tissue, obtained by the method described herein, as well as pharmaceutical products comprising such a concentrate, and use thereof in therapies for treating mammalian diseases.

In the context of this document, the expression "stem cells" is a synonym of multipotent stem cells, mesenchymal stem cells, medicinal signaling cells, stromal mesenchymal cells and adult stem cells.

BACKGROUND OF THE INVENTION

It is known that stem cells are able to subdivide for indefinite periods in culture, and to differentiate into specialized cells. They can also give rise to many types of differentiated cells and be used to treat many types of diseases.

The existence of adult stem cells in adipose tissue of mammals is also known. Such cells have already been isolated and cultivated to be used in cell therapies, such as transplants.

Until now, however, the existing knowledge about such stem cells has not solved many drawbacks. For example, the low productivity of multiplication processes for such cells compared to the needs of their use as well as the little understanding concerning the stem cells' composition used in cell therapies. In general, the fraction of stem cells isolated from adipose tissue is named stromal vascular fraction of adipose tissue that derives perivascular cells and which also has paracrine activity similar to mesenchymal stem cells.

Another existing problem is the large amount of stem cells needed to achieve effectiveness in various therapies, typically between $2 \times 10^6$ and $1 \times 10^7$ cells per kilogram of body weight of the patient.

Additionally, despite being multipotent, stem cells derived from adipose tissue as known in the art have been reported only in limited number of cases of use concerning treatment of certain types of diseases and tissues.

Those facts limit the use and increase the cost of stem cells derived from adipose tissue in cell therapies, regardless of the fact that such cells are more abundant than those obtained from other sources.

The present invention brings improvements and solutions to the state of the art, as it provides:

a high-productivity process for immunocompatible multipotent stem cells from vascularized adipose tissue, including culture and cell division;

a synergic concentrate of immunocompatible and multipotent cells that allows the use of a smaller amount of stem cells in a variety of therapeutic treatments of diseases in mammals (involving, for example, osteoarticular, muscular, neurological, hematological, dermatological, immuno-mediated urinary system diseases and many others).

DESCRIPTION OF THE INVENTION

Figure 1:
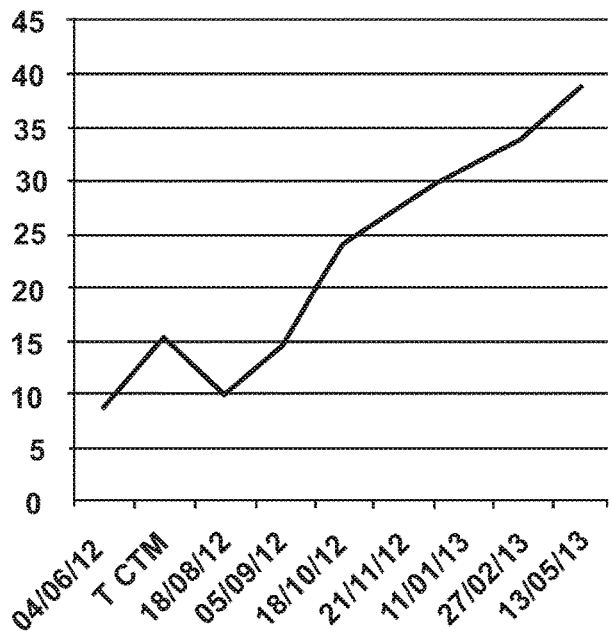
FIG. 1 is a graph of increased hematocrit levels after a single application of the cell concentrate of the invention.

In a first aspect, the present invention relates to a multipotent and immunocompatible concentrate of stem cells that secrete medicinal molecules, originated from mammalian vascularized adipose tissue, comprising: immature stem cells (ISC), mesenchymal stem cells (MSC) and perivascular cells (pericytes).

The stem cell concentrate of the invention, isolated from mammals, is immunopositive at least to CD146+, α-SMA+, CD44+, CD73+, CD90+, CD105+, CD13+, vimentin+, nestin+, Nanog+, Oct3/4+, Sox2+ markers, and immunonegative at least to CD34−, CD45−, CD56−, CD144−, CD14−, CD11b− and CD31− markers. Additionally, the stem cell concentrate of the invention isolated from humans is immunopositive to NG2+, PDGFRβ+, CD271+ (P75), CD29+, SOX9+, SOX17+, FOX2+, CD140+ markers and immunonegative to KLF4−.

Typically, the stem cell contents in the concentrate of the invention are:

ISC: 1% to 20%
MSC: 70% to 100%
Pericytes: 10% to 30%

The expression "stem cell contents" refers to the percentages of cells that express the respective markers (CTI, CTM or pericytes, respectively).

Particularly, without excluding any other alternatives, the concentrates of the invention have about 5% of ISC, 100% of MSC and 20% of pericytes, or values close to those.

The number of immature stem cells (ISC), mesenchymal stem cells (MSC) and pericytes obtained from multiple niches of stem cells of adipose tissue varies among patients and with the isolation method. Thus, mixtures of concentrates obtained from 2 or more donors may be used in order to reach average contents different from the individual contents. Alternatively, the stem cell concentrate can be enriched with specifically cultured pericytes.

The composition of cells in the concentrate of the invention is synergic, since the combined effects of ISC, MSC and pericytes unexpectedly results in the use of lesser amounts of cells compared to the amounts of stem cells currently used to achieve effectiveness in therapeutic treatments, as described further on.

Variations of the stem cell composition in the concentrate of the invention are also important since, as depending on the treatment (of a disease, trauma, injury, aesthetic-dermatological aspect, etc.), this composition can be purified and/or enriched with cells that express important markers for of the specific disease, trauma, injury or other. A therapeutic composition can be adjusted to the patient needs concerning the ratio of markers that are expressed by the cells in the concentrate, as well as regarding the dosage of stem cells, that is, a personalized medicine is proposed.

The cell concentrate of the invention can be used in the non-differentiated state of its stem cells, or the cells can be induced to produce the precursors of specific lineages (for example, glial cells) of interest for the treatment, which can be purified and applied as a pure population of precursors that are committed to a single type cell differentiation for the benefit of the autocrine effect of these cells. On the other hand, these cells have paracrine effects generated by the cells when they are not differentiated. For a more comprehensive therapeutic effect, the composition of non-differentiated cells can be used with the precursor cells.

These precursor cells have the ability to differentiate, in vitro, at least into derivatives of two germ layers: mesoderm (bone, cartilage, muscle, etc.) and ectoderm (neural cells). However their differentiation is not limited only to mesoderm and ectoderm, since under appropriate conditions, these cells can also produce the cell types derived from endoderm, what characterizes them as multipotent cells.

The cells contained in the concentrate of the invention have similar phenotypic and functional characteristics, but distinct in many aspects (cell division, expression of some genes and proteins and paracrine action), from those within the donor organism (in vivo).

There are significant differences between the cell lines in the concentrate of the invention and in the in vivo adipose tissue. Post-differentiating levels of the factors leptin and TNF-alpha secreted in cultures (in vitro) of adipose tissue cells are much lower in comparison with the in vivo tissue. In addition, an important early regulator of the adipogenesis transcription, KLF4, has significantly higher expression in vivo than in vitro. Thus, it is not a matter of mere isolation of stem cells, as they are found in the body tissue of the donor, but of removing, treating and growing them specifically to attain unpredictably improved characteristics, adequate to the therapeutic purposes of the invention.

The stem cell concentrate of the invention does not induce immune response, thus being able to be used in autogenous transplants (the patient is the donor and the receptor), allogeneic transplants (the donor is related or pertains to the same species of the patient) and xenogeneic transplants (stem cells from different, unrelated species).

Moreover, the use of the inventive cell concentrate in therapeutic treatments does not generate side effects, such as those typically found in traditional therapeutic treatments that employ synthetic compounds, whether in the short or long term.

The stem cell concentrate of the invention is particularly suitable for cell therapies, particularly cell transplants. The stem cell concentrate of the invention can derive a wide spectrum of tissues derived from the three embryonic germ layers (mesoderm, ectoderm and endoderm).

A particular aspect of the invention relates to the standardization sought in its various aspects, to ensure the success of the attained effects, whether with regard to the large production of cells from vascularized adipose tissue or to the potency and therapeutic efficiency obtained with the use of smaller amounts of cells compared to the state of the art.

An important aspect of the invention is the quality of the donor, source of adipose tissue. In the veterinary field, the isolation of stem cells from healthy young animals provide effective results of high productivity, potency and therapeutic efficiency in comparison with the isolation of cells from adult and/or old animals, or chronically ill, what provides less satisfactory effects. Thus, for optimized embodiments of the invention, the appropriate age of the donor mammal is between 20% and 30% of its full life cycle. Particularly for dogs and cats as donors of vascularized adipose tissue, the optimal range of donor age is 2-3 years. For horses, up to 6-7 years.

Still concerning the veterinary field, a suitable body region of choice for adipose tissue harvesting biopsy is the lateral region of the flank or the lateral surface of the hind limb, but the harvest is not limited to these regions, provided that the collection of vascularized adipose tissue is performed. Advantageously, the harvesting of adipose tissue can be performed during elective surgical procedures in dogs and cats—for example, castration of females (ovary salpingo hysterectomy) and pre-scrotal and inguinal castration of males. This avoids the need for a specific surgical procedure to harvest samples, avoiding more pain and suffering of the patient. For enhanced productivity of the process to obtain the stem cell concentrate of the invention, it is sufficient to harvest a small fragment of vascularized visceral fat, for example, between 0.1 and 0.3 cm$^3$, such as a fragment of about 0.5×0.5×0.5 cm. The small size of the extracted sample also facilitates, when necessary, the transportation of the sample to the laboratory (for example, using a kit adapted for this purpose) and its preservation until the beginning of in vitro cell isolation.

The stem cell concentrate of the invention can be cryopreserved, in a manner per se known to one skilled in the art, to be stored for later use, when it will be submitted to a thawing procedure, also known to the person skilled in the art. For example, the stem cell concentrate of the invention can be frozen in cryotubes in concentrations of $1 \times 10^6$, $2 \times 10^6$ or any other, and kept at −80° C. for 3 months, later transferred to liquid nitrogen at −196° C. The culture medium used to cryopreserve cells keeps them viable and preserves their differentiation potential, for example, when comprised of 45% DMEM-h (Dulbecco's Modified Eagle Medium—high glucose), 45% of fetal bovine serum and 10% of dimethyl sulfoxide.

With respect to the use of the invention in the veterinary field, concerning the aspect of health of the animal donor of adipose tissue, it is advantageous, to ensure optimized effects of the invention, that the animals (particularly dogs, cats and horses) are up to date with vermifugation against nematodes and cestodes and already vaccinated against:

dogs: canine distemper virus, hepatitis, parovirus, 4 strains of leptospirosis, parainfluenza, coranivirus, parainfluenza, laryngotracheitis, giardia, cough of the kennels and rabies;

cats: rhinotracheitis virus, calicivirose, panleukopenia, feline leukemia, chlamydiosis and rabies.

horses: rabies virus, equine influenza, encephalomyelitis.

In another aspect, the invention relates to the use of the stem cell concentrate of the invention in the preparation of products useful in treating diseases, trauma, injuries, aesthetic-dermatological aspects, etc., with stem cell transplantation. Without excluding any other alternatives, examples of such products are biopharmaceuticals, solutions, tablets, ophthalmic formulations, topical or mucosal formulations, etc.

In another aspect, the invention relates to biopharmaceuticals, characterized in that they comprise said stem cell concentrate and one or more biologically acceptable ingredients, e.g., saline solution, biomaterials (for example, polymeric biomaterials), growth factors (for example, VEGF, TGF-beta, ITK), mono-nuclear cells, platelet-rich plasma, fibrin, collagen membranes, hydroxyapatite, bioactive molecules (for example, hormones and mitogens). Particularly, a formulation for injection contains at least the stem cell concentrate of the invention and saline solution.

The invention takes advantage of particular aspects of the process of obtaining the synergistic concentrate of stem cells, for example, the isolation of a greater amount of stem cells from multiple niches of adipose cells in the same tissue fragment, which in explant culture releases in vitro unlimited amounts of stem cells in culture. Thus, the fragments of the adipose tissue initially plated in culture bottles can be transferred to new culture bottles to maintain the release of new stem cells.

Thus, without excluding any other alternative, an advantageous process for obtaining the synergistic composition of the stem cells of the invention comprises the following steps:

A—obtaining a sample vascularized adipose tissue from a mammal, particularly of a young and healthy mammal;
B—washing and cleaning of the tissue sample, for example, with saline and antibiotics;
C—performing fragmentation of the tissue sample;
D—mild enzymatic digestion of the fragments of adipose tissue to eliminate adipocytes, until inactivation of the enzyme, for example, collagenase types I or IV;
E—centrifugation to obtain cells from the vascular fraction of adipose tissue;
F—culturing of tissue explant—particularly 5 to 7 tissue fragments per 25 cm$^2$ bottle of adherent material, from 3 to 5 days, without changing the culture medium;
G—when reaching confluence between 70 and 90%, dissociate via enzymatic action the cell colonies that migrated out of the tissue;
H—optionally, the tissue separated in step E can be subjected to a new explant culture, starting a new step F;
I—culturing of isolated cells in step G, particularly up to a maximum of 6 times for later use in cell therapy.

After step A, the harvested tissue sample is cleaned and washed and may be placed in a container that serves as a temporary storage medium for transportation to another location for up to 48 hours. There are kits known in the state of the art for this purpose.

As already mentioned, to ensure optimal results of the invention, the vascularized adipose tissue mammal donor is young and healthy. Advantageously, the age of the donor should be up to a maximum of 30% of its total life cycle, preferably up to 20%. The health should preferably be such that essentially excludes any disease.

The process used allows avoiding any type of cell fluid filtration, or avoids any type of cell selection using size, granularity or specific markers, for example, magnetic beads and specific antibodies.

One aspect of the enzymatic digestion of the adipose tissue in step (D) is that vessels or fat from the sample are not discarded after digestion. The enzyme is suitable for smooth digestion of the connective tissue, for example, type I or type IV collagenase, such as the product GIBCO©, available from Life Technologies, a USA company.

If it is desired to enrich the stem cell concentrate of the invention with pericytes, the blood vessels obtained from the smooth digestion are separated from the sample of adipose tissue, and the explant growth is performed only with them, according to steps F, G and I. The pericytes then obtained can be added, in a later moment, to the concentrate to be enriched.

In step F, it is preferred that the culture medium is not changed during 3-5 days, and the equivalent amount of the evaporated medium may be replenished. The maintenance of the culture medium during this time provides selection only of cells that can be adhered to the plastic of the culture bottle, a characteristic of mesenchymal stem cells. The confluence between 70 and 90% allows the isolation of multiple colonies of fusiform cells with mesenchymal morphology and substantially standardized size.

To favor good performance of the concentrate of the invention, the growth medium in step F should be of high quality, that is, standardized with minimal variation of its pre-identified components. An appropriate example of such medium, without excluding any other, is DMEM-h (Dulbecco's Modified Eagle Medium-high glucose), commercialized as GIBCO©, available from Life Technologies, a US company, supplemented with 15% of fetal bovine serum from Hyclone, a US company, supplemented with 15% fetal bovine serum from the US company Hyclone, 1% of L-glutamine, 1% of non-essential amino acids and 1% of a penicillin/streptomycin mixture to neutralize collagenase, all other ingredients from Life Technologies, a US company.

In step H, the fragment of the adipose tissue in culture can be transferred multiple times in the culture bottle, particularly up to 5 times, still releasing cells.

It is verified that, in phase I, the culture of cells up to 6 passages is aimed at the safe use in cell therapy, avoiding the induction of changes in the karyotype, proliferation or undifferentiated state. For other applications in basic and applied science, the number of passages can be higher than six passages.

In another aspect, the invention refers to stem cell concentrates as described, characterized in that they are for use in medical, veterinary or cosmetic therapy.

In another aspect, the invention relates to the use of the stem cell concentrate of the invention in therapies (autologous, heterologous and xenotransplants) in the treatment of mammal diseases, such as joint, neurological, hematological, ophthalmic and kidney (acute and chronic) diseases, musculoskeletal disease, diabetes and acute spinal cord injury.

Particularly in the veterinary field, pathology therapies can still be cited, without excluding any other, such as:
hematopoietic diseases (medullary hypoplasia and aplasia)
joint diseases (hip dysplasia, osteoarthritis, degenerative process)
bone fissures, gaps and fractures
tendon and ligament laceration
keratoconjunctivitis sicca, corneal ulcer
neurological sequel derived from canine distemper virus
myeloencephalitis derived from equine protozoal
acute and chronic kidney disease
masticatory myositis
diabetes type I
atopy
purulent/necrotic skin lesion
for dogs: neurologic sequel of canine distemper and other neurodegenerative diseases, hip dysplasia, masticatory myositis;
for dogs and cats: medullary aplasia and hypoplasia; bone fractures; degenerative osteoarticular diseases, acute spinal cord injury, acute and chronic kidney disease, eye diseases (for example, retinal degeneration, keratoconjunctivitis sicca), diabetes;
for horses: tendon and ligament injuries, neurological sequel caused by encephalomyelitis virus, osteoarthritis and laminitis.

In another aspect, the present invention refers to dosage forms for the treatment of mammal diseases and, particularly, the amount of stem cell concentrate cells varies, for example, between $1 \times 10^6$ and $1 \times 10^7$ stem cells Evaluation Of Tumorigenic Potential The evaluation of tumorigenic potential of the cell concentrate of the invention was made in a manner known to one skilled in the art, for example, from information available in Cell Cycle (2009). 15; 8(16), 2608-2612 and "Teratoma formation: A tool for monitoring pluripotency in stem cell research", in www.stembook.org.

A cell concentrate of the invention with $2\times10^6$ cells was injected into the pelvic limb of 5 mice from nude lineage. The mice were kept under normal conditions for 60 days. Then, they were euthanized and no neoformed mass in the muscle or other body was observed.

EXAMPLES

Exemplary embodiments of the present invention are described below. Such examples should be considered only as illustrative of the particular embodiments of the invention, and not in a restrictive sense, without imposing limits of any type, beyond those comprised in the attached claims.

Example 1

Isolation of Stem Cells of the Invention from Adipose Tissue of Dogs and Cats

In the examples given further on, obtaining vascularized adipose tissue followed the procedure below.

Firstly, the region of choice, the lateral side of the animal hind limb, was well washed with water and soap. Then, the skin was shaved using a razor blade or knife and the region was cleaned with soap and water one more time. In the sequence, the area was cleaned with gauze moistened in degerming chlorhexidine (solution of Riohex 2% degerming chlorhexidine, commercialized by Rioquimica, a Brazilian company). This procedure was performed twice. Then, 5 ml of lidocaine (anesthetic) was applied on the harvesting region. This region was firstly isolated with surgical field cloth and then a 2-3 cm skin incision was made with a scalpel. The fat fragment was removed, measuring about $0.5\times0.5\times0.5$ cm using a scalpel and an allis forceps, in order to ensure the presence of blood vessels in the sample. After the harvesting, the site was cleaned with sterile gauze to dry possible bleedings and the skin sutured with thread, followed by disinfection after suturing, for example, with rifocin.

The collected adipose tissue was firstly washed in phosphate buffered saline solution (PBS) with 5% streptomycin/penicillin for removing blood, debris and possible contaminants present in the sample. The washing procedure was repeated 5 times. Then sterile gauze was used to remove PBS in excess contained in the sample. The tissue was transferred to a 60 mm Petri dish to perform tissue fragmentation with a scalpel blade No. 22, thus obtaining several smaller fragments. Then, 2 mL of 0.075% type I or type IV collagenase (Gibco®) were added to the culture plate and then diluted in PBS at 37° C. The fragments with collagenase were kept between 2 and 4 hours at 37° C. under a 5% $CO_2$ atmosphere. During incubation with collagenase, the sample was homogenized at least every 2 hours with a 1000 µL graduated pipette.

After this period, 5 mL of the following culture medium was added: DMEM supplemented with 15% fetal bovine serum from Hyclone, a US company, supplemented with 1% L-glutamine, 1% non-essential amino acid and 1% streptomycin/penicillin mix to neutralize collagenase (all ingredients from Life Technologies, a US company). The content was transferred to a 15 ml conical tube and centrifuged during 5 minutes at 200 g. This procedure was performed twice for the complete inactivation of collagenase. In the last centrifugation, the cells were re-suspended in 1000 µL of the culture medium already described and counted in a Neubauer chamber. Around $2\times10^6$ cells were transferred to a 25 cm² culture bottle prefilled with 4,000 µL of the same culture medium.

The cells were kept at 37° C. in 5% $CO_2$ atmosphere. After adhesion of the cells during a 3-5 day period, the culture medium was discarded and a new one was added in the bottle. After a period of 3 to 5 days, the first colonies of fusiform fibroblastoid cells were formed (counted as passage zero). After 7-9 days, the colonies reached between 70% and 90% of confluence. At this stage, the first cell replating was made by transferring the contents of a 25 cm² bottle to four 25 cm² bottles—starting the first passage—which were then replated when a confluence between 70 and 90% was reached, and were expanded ex vivo until the $6^{th}$ passage (from which a decline in the cell proliferation rate was observed). These steps ensured the isolation of the cell concentrate of the invention.

In the following examples, the cell concentrate of the invention was used, obtained according to the procedure above, containing approximately 5% ISC, 100% MSC and 20% pericytes obtained by mixing the concentrates from 3 distinct donors and was enriched with pericytes specifically cultivated (the cell obtainment and isolation was done with the procedure known by the person skilled in the art).

In the examples with equines, the sample of adipose tissue was removed from the tail or withers of the animals.

Example 2

Canine Distemper 2.1 Animals Used

The dogs used in this experiment were males and females of different races, with ages ranging from 1 to 6 years. All animals presented clinical neurological symptoms caused by invasion of canine distemper virus in the central nervous system, such as myoclonus, paraplegia, tetraplegia, paraparesis, seizure and inability to stay on feet and walk, according to Table I below. All dogs had been previously subjected to conventional treatment against the symptoms manifested in the viremic phase (digestive and respiratory) and presented no gastrointestinal and respiratory clinical symptoms. Transplants were performed with a time interval of 30 days between each application.

2.2 Pre-Transplant Clinical Evaluation

Patient anamnesis was performed and supplementary blood tests, chest x-rays and abdominal ultrasound were conducted to rule out the pre-existence of neoplasms.

2.3 Transplant

Transplant of the concentrate of the invention was carried out intravenously in patients with neurologic sequel of canine distemper. The cell number varied with the animal weight (table I). Patients received on average three transplants of cell concentrate of the invention at an interval of 30 days between each transplant. This was accomplished through intravenous access with a catheter and the animal was maintained in fluid therapy with 0.9% saline solution. Previously preserved cells of the invention were thawed according to the appropriate procedure, and were re-suspended into 2 mL of 0.9% physiological solution. The infusion of stem cells was slowly carried out.

TABLE I

Neurological clinical signals of the patients

| dog | breed | Age (months) | Weight (kilos) | gender | Neurological Sequel (months) | Symptoms | No. of transplants | No. of cells per transplant |
|---|---|---|---|---|---|---|---|---|
| 1 | mongrel | 24 | 7 | M | 2 | quadriplegia | 3 | $4 \times 10^6$ |
| 2 | mongrel | 8 | 7 | F | 4 | paraplegia | 3 | $4 \times 10^6$ |
| 3 | mongrel | 15 | 3 | F | 3 | paraplegia | 3 | $4 \times 10^6$ |
| 4 | poodle | 32 | 4 | F | 3 | Inability to stand and, when supported, presented severe ataxia and paraparesis of both members | 3 | $4 \times 10^6$ |
| 5 | mongrel | 21 | 25 | M | 5 | Inability to stand and, when supported, presented severe ataxia and paraparesis of both members | 3 | $6 \times 10^6$ |
| 6 | mongrel | 36 | 3 | M | 29 | Inability to stand and, when supported, presented severe ataxia and paraparesis of both members | 2 | $4 \times 10^6$ |

2.4 Post-Transplant Clinical Evaluation

After treatment, the animals were monitored for 1 hour by the veterinarian to check for possible anaphylactic reactions. None of the patients presented symptoms of rejection after transplantation of the cell concentrate of the invention. Clinical returns were carried out in 48 hours, 7 days and 21 days after application of the stem cells and the time interval between two applications was 30 days. Most of the animals presented reduction of neurological clinical signs and were able to walk again—the less positive results occurred with the older animals and with those with more time on sequels.

Table II below shows the evolution of reduction of neurological sequel.

TABLE II

Evolution of reduction of neurologic sequel of canine distemper after treatment with cells of the invention concentrate.

| dog | D0 | D1 | D2 | D3 |
|---|---|---|---|---|
| 1 | quadriplegia | Unable to stand and support weight and, when sustained, presented mild movements of FL Ataxia and paresis. No intentional movement HL paralysis | Unable to stand and support weight and, when sustained, presented mild movements of FL and HL. Ataxia and paresis. | Unable to stand and support weight and, when sustained, presented mild movements of FL and HL. Ataxia and paresis. Normal gait |
| 2 | Paralysis | Stand and support weight, minimum gait, ataxia and paraparesis | Stand and support weight, minimum gait, ataxia and paraparesis | |
| 3 | quadriplegia | Unable to stand and support weight. mild ataxia and paraparesis of of FL and HL. moderate ataxia and paresis of HL. | Stands and supports weight, normal gait. Stands and supports the body's weight. Ataxic gait and minimal paraparesis. | Normal gait |
| 4 | Unable to stand and support weight and, when sustained, presented mild movements of FL and HL. Severe ataxia and paresis. | Unable to stand and support weight and, when sustained, presented mild movements of FL and HL ataxia and paresis. | Stands and supports weight. Mild ataxia and paresis of FL and HL. | Normal gait |
| 5 | Unable to stand and support weight and, when sustained, presented mild movements of FL and HL. Severe ataxia and paresis. | Unable to stand and support weight and, when sustained, presented mild movements of FL and HL. Moderate ataxia and paresis. | Unable to stand and, when sustained, showed mild ataxia and paresis FL and HL | Unable to stand and, when sustained, showed mild ataxia and paresis of FL and HL. |

TABLE II-continued

Evolution of reduction of neurologic sequel of canine distemper after treatment with cells of the invention concentrate.

| dog | D0 | D1 | D2 | D3 |
|---|---|---|---|---|
| 6 | Quadriplegia | Unable to stand and support weight and, when sustained, presented mild movements of FL and HL. Moderate ataxia and paresis. | Unable to stand and when sustained. Presented mild ataxia and paresis FL and HL. | Unable to stand and, when sustained, showed mild ataxia and paresis of FL and HL. |

D0 - neurological symptoms before the transplant. 1$^{st}$ transplant.
D1 - neurological symptoms after the 1$^{st}$ transplant (30 days)
D2 - neurological symptoms after the 2$^{nd}$ transplant (60 days)
D3 - neurological symptoms after the 3$^{rd}$ transplant (90 days)
fore limb = FL
hind limb = HL Example 3

Hypoplasia and Aplasia of Bone Marrow 3.1 Animals Used

A 30 Kg one-year old male Labrador retriever presented weakness, loss of appetite and severe anemia, according to the hemogram. The dog had been previously submitted to monthly blood transfusions for a period of 5 months and was being treated with exogenous erythropoietin in an attempt to keep the hematocrit levels acceptable for a canine species.

3.2 Pre-Transplant Clinical Evaluation

Dog anamnesis was performed and supplementary blood tests, chest x-rays and abdominal ultrasound were conducted to rule out the pre-existence of neoplasms. The medullar biopsy diagnosed erythroid and granulocytic hypoplasia, and megakaryocytic aplasia.

3.3 Transplant

A single transplant with $8\times10^6$ cells of the invention concentrate was performed intraosseously in the femur bone. The animal was initially sedated with 4 mg/Kg intramuscular tramadol hydrochloride (a pre-anesthetic medication), followed by the induction to the effect of intravenous 8 mg/kg propofol (2,6-diisopropylphenol), maintained with isoflurane (2-chloro-2-(difluoromethoxy)-1.1.1-trifluoro-ethane). Then, a broad trichotomy of lumbosacral region and antisepsis with 2% chlorhexidine were made. Then, the access to the femoral crest was performed with a specific needle for spinal biopsy. Cryopreserved cells of the invention were thawed, re-suspended in 1 ml of 0.9% physiological solution and the infusion of stem cells was carried out slowly.

3.4 Post-Transplant Clinical Evaluation

Clinical returns were carried out with peripheral blood collection for hematocrit control and general physical examination, at intervals of around 30 days. The patient did not express symptoms of rejection after transplant with the cells of the invention. After a single transplant with the concentrate cells of the invention, the dog did not need to receive blood transfusion for one year—after this year, the aspirate examination of the bone marrow indicated a hematopoietically active bone marrow with a erythroid series slightly augmented, with normal morphology, complete and orderly maturation and predominance of mature forms, whereas the myeloid series was slightly decreased, with normal morphology, complete and orderly maturation and predominance of mature forms. The animal remained well without receiving transfusion since then (until the priority filing date of this patent application).

Figure 2:
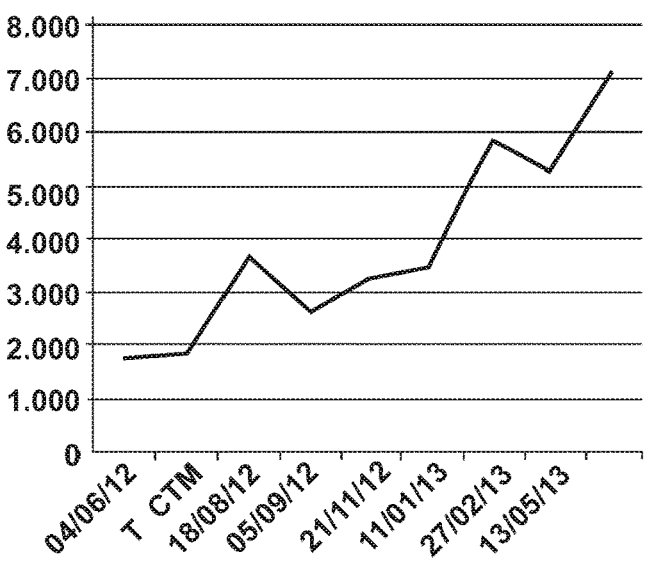
FIG. 2 is a graph of increased leukocyte levels after a single application of the cell concentrate of the invention.
Figure 3:
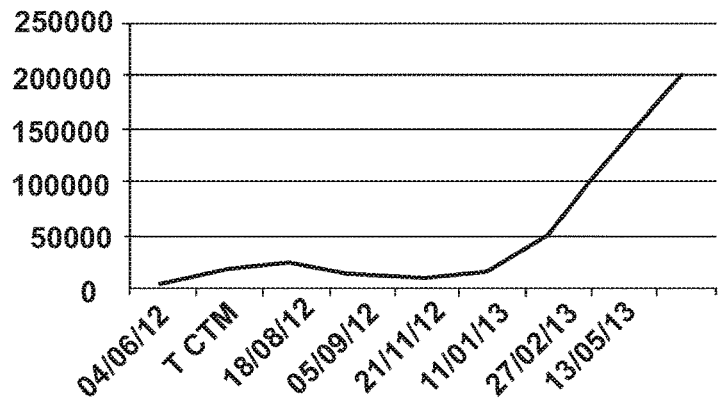
FIG. 3 is a graph of increased platelet levels after a single application of the cell concentrate of the invention.

The graphics of FIGS. 1, 2 and 3 present a significant increase of hematocrit levels (FIG. 1), leukocytes (FIG. 2) and platelets (FIG. 3) after a single application of the inventive cells. The blood tests were carried out with 30 day intervals.

Example 4

Type I Diabetes 4.1 Animal Used

A 2-year 8 Kg female dog with high levels of blood glucose and earlier diagnosed of type I diabetes.

4.2 Pre-Transplant Clinical Evaluation

Patient anamnesis was performed and supplementary blood tests, chest x-rays and abdominal ultrasound were conducted to rule out the pre-existence of neoplasms. The glucose test was performed twice daily, confirming type I diabetes. To reduce blood glucose levels, 3 to 6 units of insulin were being administered to the patient daily.

4.3 Transplant

Four transplants of $4\times10^6$ cells of the inventive concentrate were performed intravenously at 30 days intervals between each transplant. For this, the cryopreserved cells of the invention were thawed and re-suspended in 1 mL of 0.9% physiological solution. Intravenous infusion of stem cells was carried out slowly.

4.4 Post-Transplant Clinical Evaluation

After the transplant, the glucose test was conducted twice daily for 60 days in order to track the reduction of glucose level. The results showed a reduction in blood glucose levels and insulin dose reduction.

Figure 4:
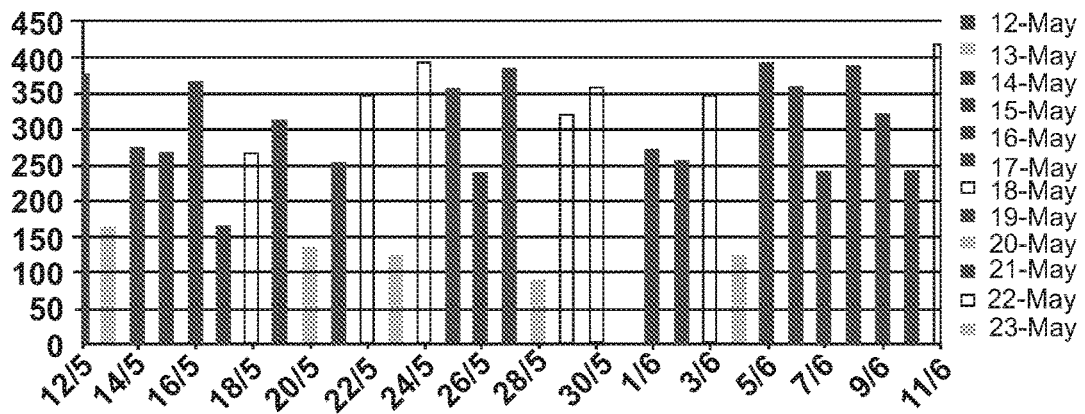
FIG. 4 is a graph of glycemic level variation in the animal prior to treatment with the cell concentrate of the invention.
Figure 5:
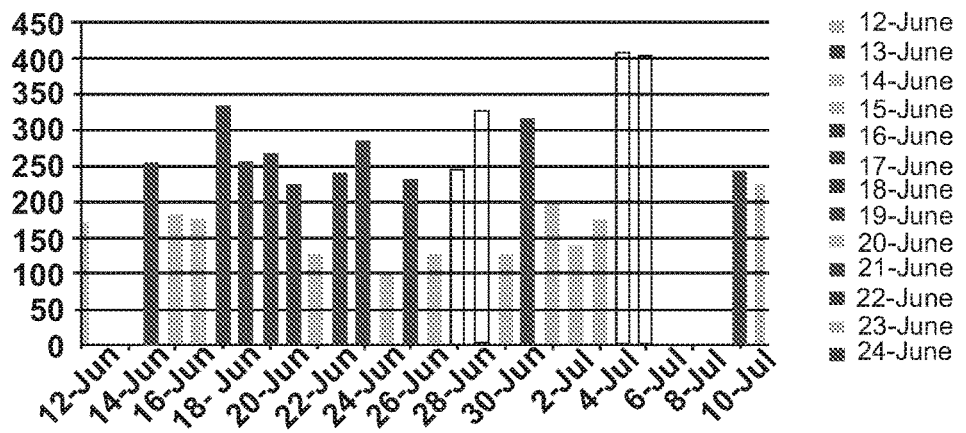
FIG. 5 is a graph of glycemic level variation in the animal after treatment with the cell concentrate of the invention.
Figure 6:
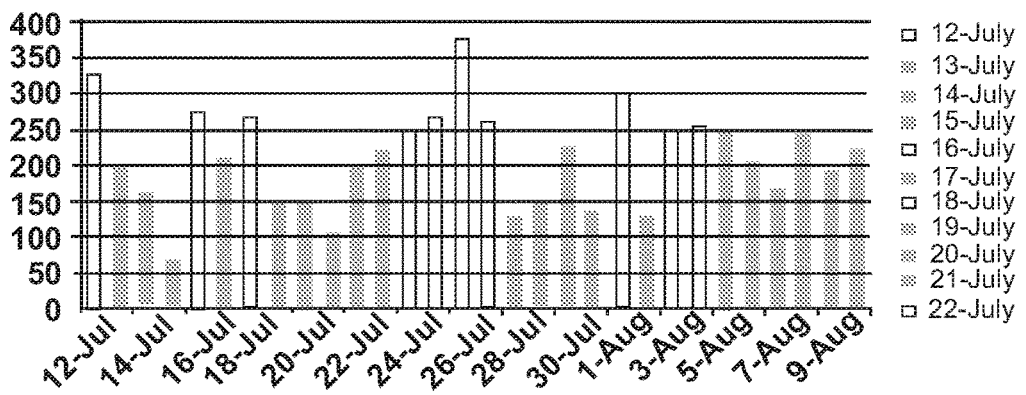
FIG. 6 is a graph of glycemic level variation in the animal after the second transplant with the cell concentrate of the invention.

In FIGS. 4, 5 and 6, letter "T" means date of the transplant.

FIG. 4 is a graph of the variation of glucose level of the animal before the treatment with stem cells. The gray color indicates the day that the patient did not receive insulin, the dark gray color indicates that the patient received 3 units of insulin per day, the white color indicates that the patient received 6 units of insulin once a day.

FIG. 5 is a graph of the variation of glucose level of the animal after the treatment with the stem cells. The reductions in the number of days without insulin and of the dose were observed. The light gray color indicates the day in which the patient did not need to receive insulin, the dark gray color indicates that the patient received 3 units of insulin, the white color indicates that the patient received 6 units of insulin once per day. It is noted that the number of days without insulin increased, as well as the reduction of the number of days when the dog needed to receive 6 units of insulin.

FIG. 6 is a graph of the variation of glucose level of the animal after the second transplant with the stem cells. A great reduction of the number of days without administering insulin and of the dose is noted. The gray color indicates the day when the patient did not receive insulin, the white color indicates when the patient received 3 units of insulin.

It is noted that after the second transplant, there was a reduction of the daily dose of insulin from 6 to 3 units per kilo. Additionally, the interval of days without having to take insulin increased.

Example 5

Masticatory Myositis

5.1 Animal Used

A 11 year male labrador retriever dog showed inability to open the mouth, along with swelling and difficulty to feed.

5.2 Pre-Transplant Clinical Evaluation

Patient anamnesis was performed and supplementary blood tests, chest x-rays and abdominal ultrasound were conducted to rule out the pre-existence of neoplasms. The biopsy of masticatory muscle indicated myositis of the masticatory muscles. The jaw opening of the animal was of 2.7 cm. The dog had been medicated with corticosteroids, but did not adapt to this treatment.

5.3 Transplant

Three transplants of $8\times10^6$ stem cells of the inventive concentrate were performed intravenously with 30 day intervals between each transplant. For this, cryopreserved cells of the invention were thawed, re-suspended in 1 mL of 0.9% physiological solution, and intravenous infusion of stem cells was performed slowly.

5.4 Post-Transplant Clinical Evaluation

After the transplant the animal showed more disposition, and was able of feed alone and to use the mouth to catch objects, what was previously not possible. The jaw opening capacity was amplified to 4.7 cm.

Example 6

Tendon Injury of Athlete Horses

6.1 Animals Used

Three male horses with ages ranging from 16 to 28 years showed focal lesions in the superficial digital extensor tendon. The lesions were diagnosed with an ultrasound machine, and classified according to the loss of linear pattern of the tendon fiber, as proposed by Nixon et al., (Nixon A J, Goodrich L R, Scimeca D M, Witte T H, Schnabel L V, Watts A E, et al. Gene therapy in musculoskeletal repair. Ann N Y Acad Sci 2007; 1117:310-327) in a scale from 1 to 4. The loss of linear pattern of the tendon fiber corresponding to 10 to 20% was classified as grade 1, while injuries between 25 to 50% were classified as grade 2.

In the table below, animals treated with the cell concentrates of the invention are cited, as well as their respective classifications of the scale of linear pattern of the tendon fiber and, according to the tendon lesion, the number of cells used in the transplant.

TABLE 1

Animals submitted to transplant with the stem cell concentrate of the invention (according to example 1, with equines being the donors of adipose tissue), percentage of injury and No. of transplanted cells.

| Animal | % of injury | Total number of transplanted cells |
|---|---|---|
| 1 | 10 | $6 \times 10^6$ |
| 2 | 20 | $8 \times 10^6$ |
| 3 | 30 | $8 \times 10^6$ |

6.2 Transplant

The animals were subjected to trichotomy followed by antisepsis with povidone-iodine, for further transplant of the cell concentrate of the invention. The application route of the cell concentrated was at the site of injury, made possible with an ultrasound which allowed the exact identification of the injury. The cell concentrate of the invention (horses were the adipose tissue donors) was applied with the aid of a 40×12 needle and 3 mL syringe. A single cell transplant was performed.

6.3 Clinical Evaluation of the Injury after Transplant

After 15 days, an evaluation of the stem cell transplant of the inventive concentrate was performed on the injured tendon site, with ultrasound.

A reduction of the injury extension of the tendon tissue and the arrangement of collagen fibers were verified. A significant improvement in the linear pattern of collagen fibers was observed.

Example 7

Acute and Chronic Kidney Disease

7.1 Animal Used

A 13-year old female pinscher dog with a history of poor appetite and low weight. The biochemical examination verified high levels of urea (86 mg/dL) and creatinine 2 (54 mg/dL). The patient was receiving fluid therapy twice a day and 2 mL of oral serum, with special diet for kidney patient with Royal renal (pâté and feed) and white meat (chicken). The drug protocol used was: Ketosteril (amino acids and analogues, marketed by Fresenius, a Brazilian laboratory), Glutamax (glutamine supplement, marketed by Vitafor, a Brazilian laboratory), omeprazole, bromopride and Hemolitan (vitamin supplement marketed by Vetnil, a Brazilian laboratory).

7.2 Pre-Transplant Clinical Evaluation

Patient anamnesis was performed and supplementary blood tests, chest x-rays and abdominal ultrasound were conducted to rule out the pre-existence of neoplasms. The biochemical test and urinalysis were also made, indicating chronic kidney disease.

7.3 Transplant

Two transplants of $2\times10^6$ cells of the inventive concentrate were performed intravenously with 30-day intervals. Cryopreserved cells of the invention were thawed and re-suspended into 2 mL of 0.9% physiological solution. The infusion of cells of the invention was slowly carried out. The patient kept the conventional treatment for the disease during the treatment with stem cells.

7.4 Post-Transplant Clinical Evaluation

Clinical returns were carried out in 48 hours, 7 days and 21 days after the transplant with the stem cell concentrate of the invention, and the interval between applications was 30 days. The patient did not express symptoms of rejection after cell transplant of the invention. The biochemical tests and urinalysis conducted showed a reduction in blood levels of urea and creatinine, ionized calcium and the increase in hematocrit, as shown in the table below.

TABLE

Values of renal function before and after the transplant.

| Dates | D0 Apr. 12th, 2012 | D1 Apr. 13th, 2012 | D1 Apr. 13th, 2012 | May 17th, 2012 | D2 Jun. 13th, 2012 | Jun. 14th, 2012 | Jun. 18th, 2012 | Aug. 28th, 2012 | Sep. 21st, 2012 | Typical values |
|---|---|---|---|---|---|---|---|---|---|---|
| No. of transplanted cells | | $2 \times 10^6$ | $2 \times 10^6$ | | $2 \times 10^6$ | | | | | |
| Urea mg/dL | 86 | | 78 | | 51 | | | | 34 | 10-50 mg/dL |
| Creatinin mg/dL | 2.54 | | 2.12 | | | 1.82 | | | 1.7 | 0.5-1.5 mg/dL |
| Hemogram (%) | 25 | | 43 | | | 38 | | 45.4 | | 50-53% |
| Ionized calcium mg/dL | | | | 6.08 | | | 6.13 | 4.96 | | 4.5-5.7 mg/dL |
| Potassium mEg/dL | | | | 5.6 | | | 4.3 | 5.1 | | 3.7-5.8 mEq/dL |
| Sodium mEg/dL | | | | | | | 155.00 | 150 | | 141-153 mEq/dL |
| Phosphorous mg/dL | | | | 5.7 | | | 3.21 | 5.3 | | 2.2-5.5 mg/dL |
| Albumin | | | | 3.15 | | | | 3.4 | | |

D0 - laboratory data before the 1st transplant.
D1 - laboratory data after the 1st transplant (30 days)
D2 - laboratory data after the 2nd transplant (60 days)

8. Treatment of Spinal Disc Extrusion

8.1 Animal Used 9 year-old 39 kg male Doberman dog showed absence of deep pain and paraplegia.

8.2 Pre-Treatment Clinical Evaluation

Patient anamnesis was performed and supplementary blood tests, chest x-rays and abdominal ultrasound were conducted to rule out the pre-existence of neoplasms, and it was observed, by magnetic resonance imaging, the spinal disc extrusion in the toraco-lumbar region at T12-13 T13-1.

8.3 Transplant

After 21 days, the spinal disc extrusion at the toraco-lumbar region was verified. During this period (21 days), a single transplant of $4 \times 10^6$ stem cells of the inventive concentrate was performed. Cryopreserved cells of the invention were thawed and re-suspended into 1 mL of 0.9% physiological solution. The infusion of stem cells was slowly carried out into the epidural space using a 3 mL syringe a 20×5.5 needle. After stem cell therapy, tramal and dipyrone were administered during 5 days and cephalexin was administered during 14 days. On the 10th day after transplant, the animal underwent physiotherapy for a period of 60 days, three times a week, and acupuncture once a week.

8.4 Post-Transplant Clinical Evaluation

Clinical returns were carried out in 48 hours, 7 days and 21 days after the transplant with the stem cell concentrate of the invention. The patient did not express symptoms of rejection after the transplant. After 30 days from transplant, the animal could stand with some difficulty walking and, after 60 days, the animal was walking normally.

Example 9

Tendon Laceration

9.1 Animal Used

A 42 kilo female german shepherd dog, with injury on left foot caused by trauma. The animal had difficulties in locomotion due to inability to support the left paw on the ground.

9.2 Pre-Transplant Clinical Evaluation

The rupture of the common calcaneal tendon was observed by ultrasound.

9.3 Transplant 28 days after the traumatic rupture of the tendon, the tendon suture was performed and, at the time of surgery, the concentrate of the invention was applied having $2 \times 10^6$ stem cells of the inventive concentrate.

9.4 Post-Transplant Clinical Evaluation

After 60 days an ultrasound was performed and the complete tendinous fibers organization was observed, the animal recovering the motor activity.

10. Keratoconjunctivitis Sicca

10.1 Animal Used

A two-year old male crossbreed dog, which featured production deficiency of tear in the left eye, during 6 months.

10.2 Pre-Treatment Clinical Evaluation

The patient anamnesis was performed and the Schirmer tear test disclosed a level of tear production of 5 mm.

10.3 Transplant

A single transplant of the stem cell concentrate of the invention was conducted subconjuntivally in the main lacrimal gland and in the lacrimal gland of the third eyelid. Cryopreserved cells of the invention were thawed and re-suspended into 0.5 μL of 0.9% physiological solution, 0.3 μL was transfused in the main gland and 0.2 μl in the gland of the third eyelid of the patient. During the treatment, only artificial tears in the first 7 days after the beginning of stem cell transplant were used.

10.4 Post-Transplant Clinical Evaluation

The clinical returns were carried out 7, 14 and 21 days after the transplant with the cells of the invention. The patient did not express symptoms of rejection after the cell concentrate transplant of the invention. After 7 days, the patient did not use artificial tears anymore and the Schirmer tear test was 10 mm, and after 14 and 21 days, it was 15 mm, which are considered normal values.

11. Ulcerative Keratitis

11.1 Animal Used

A 8-year old female Schnauzer dog presented a great width of bullous ulcerative keratitis in the right eye.

11.2 Pre-Treatment Clinical Evaluation

The patient's anamnesis was performed, and on inspection, the bullous ulceratitis of large span was observed in the right eye. Before the treatment with stem cells, the patient was treated with antibiotics during 7 days.

11.3 Transplant

Five transplants of stem cell concentrate of the invention were performed along 5 days, directly on the ulcerated cornea, with $1 \times 10^6$ cells re-suspended in 5 μL of saline solution. Cryopreserved cells of the invention were thawed before use.

11.4 Post-Transplant Clinical Evaluation

After a month of treatment with the stem cell concentrate of the invention, the cornea transparency was observed. When performing the visual acuity test (the test threat) the animal manifested reaction, and therefore, it was considered positive to the test.

Example 12

Neurologic Sequel Derived from Equine Protozoal Myeloencephalitis (EPM)

12.1 Animal Used

A 10-year-old female of the equine species, undetermined race, positive serology for Sarcocystis neuroma (title>80) with clinical signs of motor discoordination, loss of balance and gait with compromise of mainly the hind limbs.

12.2 Pre-Treatment Clinical Evaluation

For 6 months the patient presented motor discoordination, loss of balance and gait, with mainly the hind limbs compromised (severe gait ataxia). The viremic phase of the EPM was not in course (sorologic examination for Sarcocystis neuroma—title <80)

12.3 Transplant

A total of $8 \times 10^6$ cells was transplanted via epidural (sacro-coccygeal epidural space) in the horse with the neurological sequel. The cells were previously thawed and re-suspended into 2 mL of physiological solution and then transplanted via intrathecal administration.

12.4 Post-Transplant Clinical Evaluation

Twenty days after the first transplant the animal had a reduction on of the clinical signs of ataxia, motor discoordination and loss of balance, with marching ability recovery. After treatment the animal presented only light gait ataxia.

Example 13

Atopy

13.1 Animal Used 7 year-old male golden retriever, diagnosed with atopy at the age of one. The animal was treated with cyclosporine, corticoid and hypoallergenic topic treatments, with no effective response after diagnosis.

13.2 Pre-Treatment Clinical Evaluation

The dog presented severe clinical signs of atopy, such as: pruritus level 9, pyoderma, otitis, and mutilation of the elbows due to intense pruritus.

13.4 Transplant

Three transplants with $8 \times 10^6$ cells were performed intravenously, with 30-day intervals. The cells were re-suspended in 3 ml of physiological solution and injected with the aid of a 3 ml syringe with a 24×12 needle.

13.4 Post-Transplant Clinical Evaluation

The animal presented progressive improvement after the transplants. 30 days after the initial transplant the animal showed pruritus reduction. The other symptoms showed reduction after the $3^{rd}$ application (pruritus, pyoderma, otitis). After the end of the treatment the animal presented controlled atopy symptoms, without medication, with use of allergenic shampoo.

14. Treatment of Cutaneous Wounds

14.1 Animal Used

A dog 19 month-old 12 kg mongrel, female presenting tissue necrosis in the lower dorsal region and left lateral flank, with high level of pain.

14.2 Pre-Treatment Clinical Evaluation

Clinical diagnostic of necrotizing cutaneous wound, with abundant purulent secretion and significant tissue loss. Animal had been treated for 40 days with antibiotics and topical skin healing solutions, without effective results.

14.3 Transplant

Five consecutive cell transplants were performed. The first transplant was performed via three different ways: endovenous, local injection and topical (direct application on the skin would). For this treatment a total of 8×106 cells of the invention were used, divided as follows: 4×106 cells were applied intravenously, 4×106 cells equally divided between local injection and topical application.

14.4 Post-Transplant Clinical Evaluation

The animal had significant improvement after the treatment with the invention cells. Initially one observed reduction of the inflammatory process (6 days) and of the tissue necrosis (15 days). The reepitalization process was accelerated and after 60 days all affected cutaneous area was reepitelized (neoformed cutaneous tissue).

With the aid of the teachings and examples disclosed herein, the person skilled in the art can carry out the invention in equivalent forms, i.e. not expressly described, but whose functions and results are of the same nature as those of the invention, therefore within the scope of the appended claims.

The invention claimed is:

1. An isolated multipotent and immunocompatible concentrate of stem cells obtained from mammalian vascularized adipose tissue, comprising 10 to 30% pericytes immunopositive to CD146+, α-SMA+, NG2+, PDGFRβ+, CD140a+ markers, 70 to 100% mesenchymal stem cells immunopositive to CD271+ (P75), CD44+, CD73+, CD90+, CD105+, CD13+, vimentin+, nestin+, CD29+ markers, and immunonegative to CD34−, CD45−, CD56−, CD144−, CD14−, CD11b−, CD31− and CD31 markers, wherein the composition comprises 1 to 20% immature stem cells immunopositive to Nanog+, Oct3/4+, SOX2+, SOX9+, SOX17+, and FOX2+ markers and immunonegative to the KLF4− marker;

wherein said concentrate is obtained by a process comprising:
(A) obtaining a sample of vascularized adipose tissue from one or more healthy young mammals;
(B) washing and cleaning of the tissue sample;
(C) fragmentation of the tissue sample;
(D) mild enzymatic digestion of fat from tissue fragment;
(E) centrifugation to separate the tissue;
(F) culture of tissue explant during 3 to 5 days, without changing the culture medium;
(G) when reaching confluence of 70-90%, after 7-9 days, dissociate the cell colonies that migrated out of the tissue;
(H) optionally, the tissue separated in (E) can be subjected to a new explant culture, starting a new (F), and
(I) culture of cells isolated in (G).

2. The concentrate according to claim 1, wherein the mammal donor of vascularized adipose tissue has 20% to 30% of the maximum life cycle of such mammal.

3. The concentrate according to claim 1, wherein the mammalian vascularized adipose tissue is free of diseases.

4. The concentrate according to claim 1, wherein the mammalian vascularized adipose tissue is obtained from a region or process selected from the group consisting of the side region of the flank or the side surface of the hind limb, pre-scrotal or inguinal castration of males, ovary salpingo hysterectomy castration of females for dogs or cats, and the withers or tail region for horses.

5. The concentrate according to claim 1, wherein said concentrate is in the form of biopharmaceuticals, solutions, tablets, ophthalmic formulations or formulations for topical application.

6. The concentrate according to claim 1, wherein said concentrate is prepared for systemic or local administration.

7. The concentrate according to claim 6, wherein the administration is selected from the group consisting of: intravenous, percutaneous, intraosseous, topical and intrathecal.

8. The concentrate according to claim 1, wherein said concentrate is in the form of an eyewash.

9. A method for treating mammals without neoplasm, by administering to a patient in need of treatment one or more amounts of the stem cell concentrate according to claim 1.

10. A method for treating mammals with joint diseases, musculoskeletal diseases, tendon and ligament laceration, gaps and fractures; in heterologous or xeno therapies; by administering to a patient in need of treatment one or more amounts of the stem cell concentrate according to claim 1.

11. A method for treating mammals with neurological, hematological, ophthalmic and hematopoietic diseases, acute and chronic kidney disease, diabetes, acute spinal cord injury, neurological sequel derived from canine distemper virus, masticatory myositis, or neurological sequel promoted by encephalomyelitis virus; by administering to a patient in need of treatment one or more amounts of the stem cell concentrate according to claim 1.

12. A biopharmaceutical, comprising the stem cell concentrate according to claim 1, and one or more biologically acceptable ingredients.

13. A dosage form for treating diseases, traumas, injuries or aesthetic-dermatological aspects of mammals, comprising the cell concentrate according to claim 1, wherein the concentrate contains between $1 \times 10^6$ and $1 \times 10^7$ cells.

* * * * *